(12) United States Patent
Whittington et al.

(10) Patent No.: US 8,265,741 B2
(45) Date of Patent: Sep. 11, 2012

(54) TECHNIQUE FOR DETERMINING SIGNAL QUALITY IN A PHYSIOLOGIC SENSING SYSTEM USING HIGH FREQUENCY SAMPLING

(75) Inventors: Hollis Whittington, Portland, OR (US); Dirk Muessig, West Linn, OR (US); Volker Lang, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 583 days.

(21) Appl. No.: 12/391,208

(22) Filed: Feb. 23, 2009

(65) Prior Publication Data

US 2010/0217143 A1    Aug. 26, 2010

(51) Int. Cl.
*A61B 5/04* (2006.01)

(52) U.S. Cl. ........ 600/523; 600/508; 600/509; 600/510; 600/515

(58) Field of Classification Search .......... 600/509–510, 600/515, 523
See application file for complete search history.

(56) References Cited

U.S. PATENT DOCUMENTS 5,228,450 A * 7/1993 Sellers .......................... 600/524

OTHER PUBLICATIONS

Brignole et al., "Improved Arrhythmia Detection in Implantable Loop Recorders," Journal of Cardiovascular Electrophysiology, Apr. 10, 2008, 7 pages.

* cited by examiner

*Primary Examiner* — Nicole F Lavert
(74) *Attorney, Agent, or Firm* — ARC IP Law, PC; Joseph J. Mayo

(57) ABSTRACT

A medical device for processing physiological signals such as electrocardiograms. The processing includes: sampling a physiologic signal in a first channel with a first sampling rate, simultaneously sampling the physiologic signal in a second channel with a higher sampling rate to thus generate pairs of sampling values, forming the difference between two sampling values of each pair, comparing said difference with a threshold, and generating a noise detection indicator whenever said threshold is exceeded.

17 Claims, 3 Drawing Sheets

TECHNIQUE FOR DETERMINING SIGNAL QUALITY IN A PHYSIOLOGIC SENSING SYSTEM USING HIGH FREQUENCY SAMPLING

BACKGROUND OF THE INVENTION

1. Field of the Invention

The invention relates to a heart monitor or a cardio-therapy device comprising a heart monitor, such as an implantable heart stimulator. Implantable heart stimulators include cardiac pacemakers, cardioverters/defibrillators and the like. Heart monitors include implantable devices such as physiologic recorders, loop recorders, or implantable "Holter" recorders. The invention further refers to a method of processing electrogram signals.

2. Description of the Related Art

A primary task of an implanted cardiotherapy device is the classification of signals—usually electrogram (ECG) signals—indicating the electrical activity of the human heart. More particularly, a task for a heart monitor is the accurate identification of rhythm categories. The basis of intracardiac electrogram classifiers in presently implanted devices is comparing the signal amplitude to a threshold and comparing the frequency of threshold crossings to a rate limit.

In these systems, signal noise can be a problem, since noise may be mistaken as a cardiac event and, thus, may lead to misclassification of an electrogram signal as representing tachycardia.

Implantable heart stimulators can be used for treating a variety of heart disorders like bradycardia, tachycardia or fibrillation by way of electric stimulation pulses delivered to the heart tissue, the myocardium. Tachycardia is a phenomenon where the heart exhibits a heart rate that is faster than it should be and therefore is subject to therapy. Tachycardia ventricle can be a "slow" tachycardia that is called ventricular tachycardia (VT). There is another form of tachycardia called ventricular fibrillation (VF), where the ventricle exhibits a very high rate of contractions that are uncoordinated and, thus, seriously affect the ventricle's capability to pump blood. VF therefore can be lethal if not treated quickly, e.g. by means of a defibrillator delivering a defibrillation shock.

In any case, reliable assessment of the heart rate is needed. The heart rate is the rate with which natural contractions of a heart chamber occur.

In order to be able to sense a contraction, a heart chamber excitation that naturally occurs without artificial stimulation and that is called intrinsic, the heart stimulator usually comprises at least one sensing stage that is connected to a sensing electrode on said electrode placed in the heart chamber. Electrical potentials can be picked up via the sensing electrode and can be evaluated by the sensing stage in order to determine whether an intrinsic excitation—called: intrinsic event—has occurred.

Usually, heart stimulators feature separate sensing stages for each heart chamber of interest. In a dual-chamber pacemaker, usually two separate sensing stages, an atrial sensing stage and a ventricular sensing stage, are provided that are capable to detect intrinsic atrial events AS (atrial sensed event) or intrinsic ventricular events VS (ventricular sensed event), respectively.

As known in the art, additional separate sensing and pacing stages are provided for three-chamber (right atrium RA, right ventricle RV, left ventricle LV) or four-chamber (right atrium RA, left atrium LA, right ventricle RV, left ventricle LV) pacemakers or ICDs.

In a heart cycle, an excitation of the myocardium leads to depolarization of the myocardium that causes a contraction of the heart chamber. Thereafter, the myocardium repolarizes and thus relaxes and the heart chamber expands. In a typical electrogram (EGM), depolarization of the ventricle corresponds to a signal known as "R-wave". The repolarization of the ventricular myocardium coincides with a signal known as "T-wave". Atrial depolarization is manifested by a signal known as "P-wave".

A natural contraction of a heart chamber thus can be detected by evaluating electrical signals sensed by the sensing channels. In the sensed electrical signal, the depolarization of atrium muscle tissue is manifested by occurrence of a P-wave. Similarly, the depolarization of ventricular muscle tissue is manifested by the occurrence of a R-wave. A P-wave or an R-wave thus leads to an atrial sense event AS or a ventricular sense event VS, respectively.

A R-wave or a P-wave usually is detected when a respective electrogram signal exceeds a predetermined threshold. Noise in that signal may lead to over-sensing that is sensing of "false" cardiac events that actually are nothing but noise in the signal.

A published article in the technical literature presented techniques to mitigate noise in subcutaneous ECG signals collected using an implantable recorder (Brignole et al, Journal of Cardiovascular Electrophysiology, Apr. 10, 2008). Simple detection schemes are outlined that are limited in their performance.

Solutions presented in above-cited article are susceptible to over-sensing of noise and disregarding portions of data that could otherwise be used for detection of arrhythmia (false positives for noise detection). If more than two refractory senses are detected, the device blanks until the next "true" cardiac event is detected. For detection of ECG during periods of muscular activity or excessive motion, the device could detect only noise for long periods of time and would subsequently be unable to detect arrhythmias occurring during this time.

Other methods are typically constrained by the available hardware, which is itself constrained by geometry and power. As a result, simple electronics are typically used in these devices, which do not provide extreme flexibility of signal processing and manipulation.

BRIEF SUMMARY OF THE INVENTION

It is the goal of the invention to provide a heart monitor and a method that provides a better discrimination between noise and other signal contents.

According to the invention, this goal is achieved by a heart monitor comprising an electric signal acquisition and processing stage connected or being connectable to two implantable electrodes for picking up myocardial electric signals. The electric signal acquisition and processing stage comprises two signal processing channels. A first channel comprises a first sampling stage for sampling picked-up myocardial electric signals with a first sampling rate. The first channel is adapted to process picked-up myocardial electric signal so as to generate an electrogram waveform. The second channel comprises a high frequency sampling stage for sampling at least portions of the picked-up myocardial electric signals with a second sampling rate that is higher than the first sampling rate. The portions to be sampled with the second sampling rate include at least two sampled myocardial electric signal values forming a pair of myocardial electric signal values sampled with that second sampling rate.

The second channel further comprises a differential stage connected to the high frequency sampling stage and being adapted to generate a high frequency sampling output signal representing the difference between two consecutive high frequency sampled myocardial electric signal values sampled with the second sampling rate, that is, with a sampling interval shorter than the sampling interval corresponding to the first sampling rate. A comparator is connected to the differential stage and is adapted to compare the high frequency sampled output signal with a threshold and to generate a noise detection indicator whenever the threshold is exceeded by the high frequency sampled output signal.

The object of the invention is further achieved by a method for processing electric signals representing a time course of myocardial potentials. The method comprises the steps of:

Sampling a physiologic signal in a first channel with a first sampling rate, simultaneously sampling the physiologic signal in a second channel with a higher sampling rate to thus generate pairs of sampling values, forming the difference between two sampling values of each pair, comparing said difference with a threshold, and generating a noise detection indicator whenever said threshold is exceeded.

The proposed solution will use measurement capabilities that are novel to a typical ECG recording device. While most modern recorders digitize the physiologic signal at a fixed sampling rate that has been determined from the frequency content of the cardiac signal, it is possible to make specialized measurements at a higher frequency than what is required by the cardiac signals in order to detect out-of-band signal components associated with non-cardiac processes. Examples include myopotentials arising from muscle activity, or motion artifacts arising from movement of the device within the patient's body. The presence of these signal components is a direct indicator of noise that could confound detection of the cardiac signal and associated QRS complexes.

If this noise indicator is present with or without other qualifying conditions, such as QRS amplitude changes, cardiac rate changes or morphological characteristics, the subcutaneous ECG data is considered invalid and will not be used to make diagnoses or contribute to logged statistics. If the noise indicator is not present, other tests may be used to qualify the data as valid in order to diagnose arrhythmias or other pathologies.

Preferably, the second channel is adapted to generate pairs of high frequency sampled myocardial electric signal values with a repetition rate that is different than the second sampling rate. In such embodiment, each pair of high frequency sampled myocardial electric signal values is sampled with the second sampling rate and, thus, separated in time by a second sampling interval being the inverse of the second sampling rate. Generation of such pairs of high frequency sampled myocardial electric signal values is repeated with a relatively low repetition rate, so that pairs of high frequency sampled myocardial electric signal values are separated in time by a relatively long repetition interval.

It is preferred that the repetition rate corresponds to the first sampling rate, so that, for each sampled myocardial electric signal value generated in the first channel, a pair of high frequency sampled myocardial electric signal values is generated in the second channel.

In a preferred embodiment, the heart monitor further comprises a timer that is triggered whenever the high frequency sampled signal exceeds the threshold, that is, whenever a noise indicator signal is generated. In other words: The timer is triggered by each noise indicator signal.

Preferably, the timer expires after a preset noise detection period unless retriggered by another noise detection indicator signal. During any noise detection period, an ECG signal generated in said first channel is evaluated differently than outside a noise detection period.

The first sampling rate preferably is between 200 and 300 Hz. The second sampling rate preferably is between 4 to 30 kHz.

Further preferred features are apparent from the following detailed description of a preferred embodiment.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
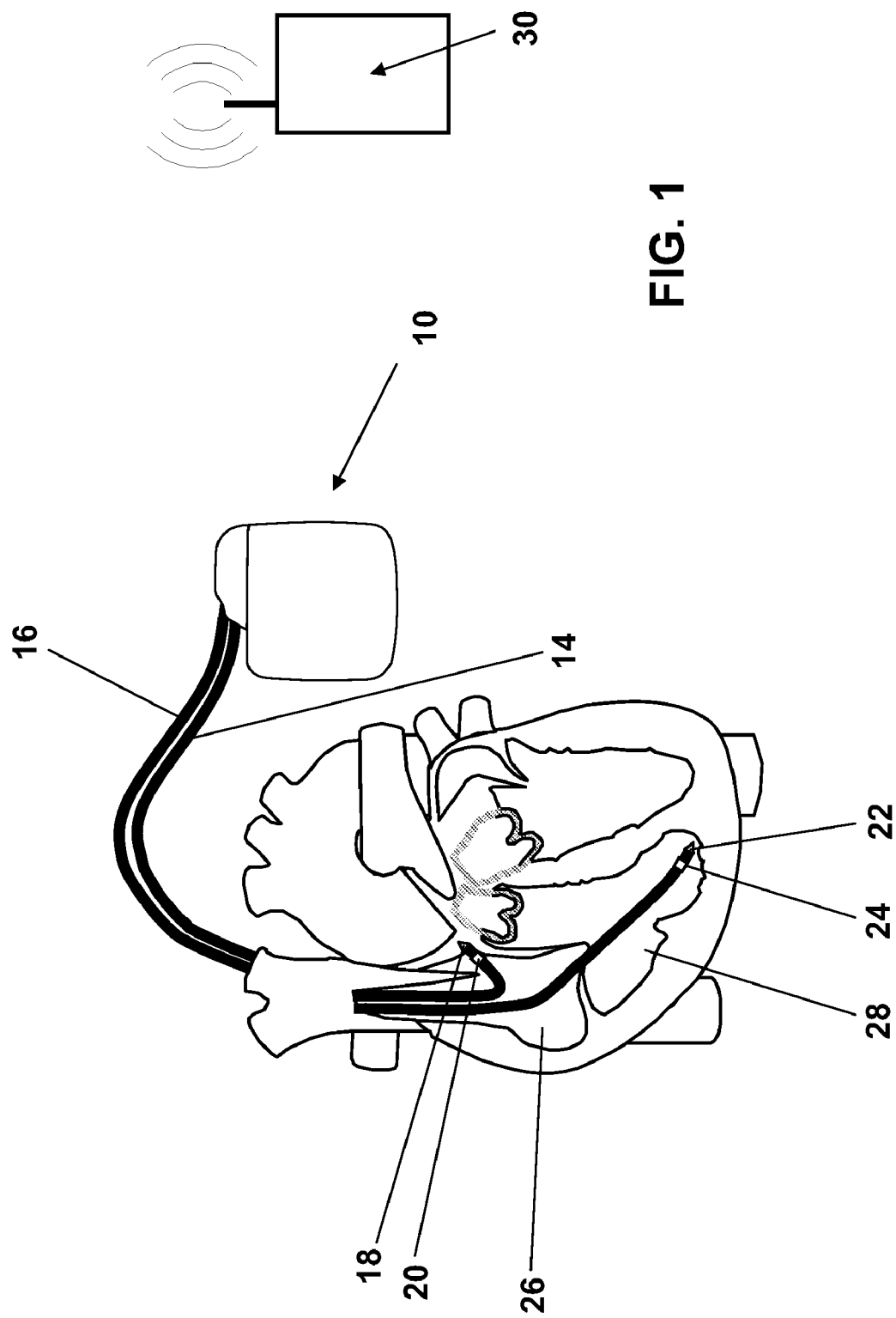
FIG. 1 shows an implantable medical device connected to electrode leads.

FIG. 1 shows an implantable medical device 10 connected to electrode leads 14 and 16 having electrodes placed in a heart.

As will be more apparent from the following description of the implantable medical device 10, the implantable medical device 10 is capable of making up intracardiac electrograms that represent electrical activity of the myocardium of either a right atrium or a right ventricle of a heart. According to further embodiments not represented in detail within this disclosure, the implantable medical device could also be capable of picking up intracardiac electrograms from the left atrium and/or or the left ventricle. Further, the implantable medical device can be made capable of creating a far field electrogram signal from intracardiac electrogram signals picked up via electrodes located at the implantable medical device 10.

In order to be capable to pick up electric potentials of the myocardium, the implantable medical device 10 (dual chamber pacemaker 10) of FIG. 1 is connected to electrode leads 14 and 16, comprising stimulation and sensing electrodes 18 and 20 and 22 and 24, respectively. Electrodes 18 and 20 are placed in the right atrium 26 of the heart whereas electrodes 22 and 24 are placed in the right ventricle 28 of the art.

Figure 2:
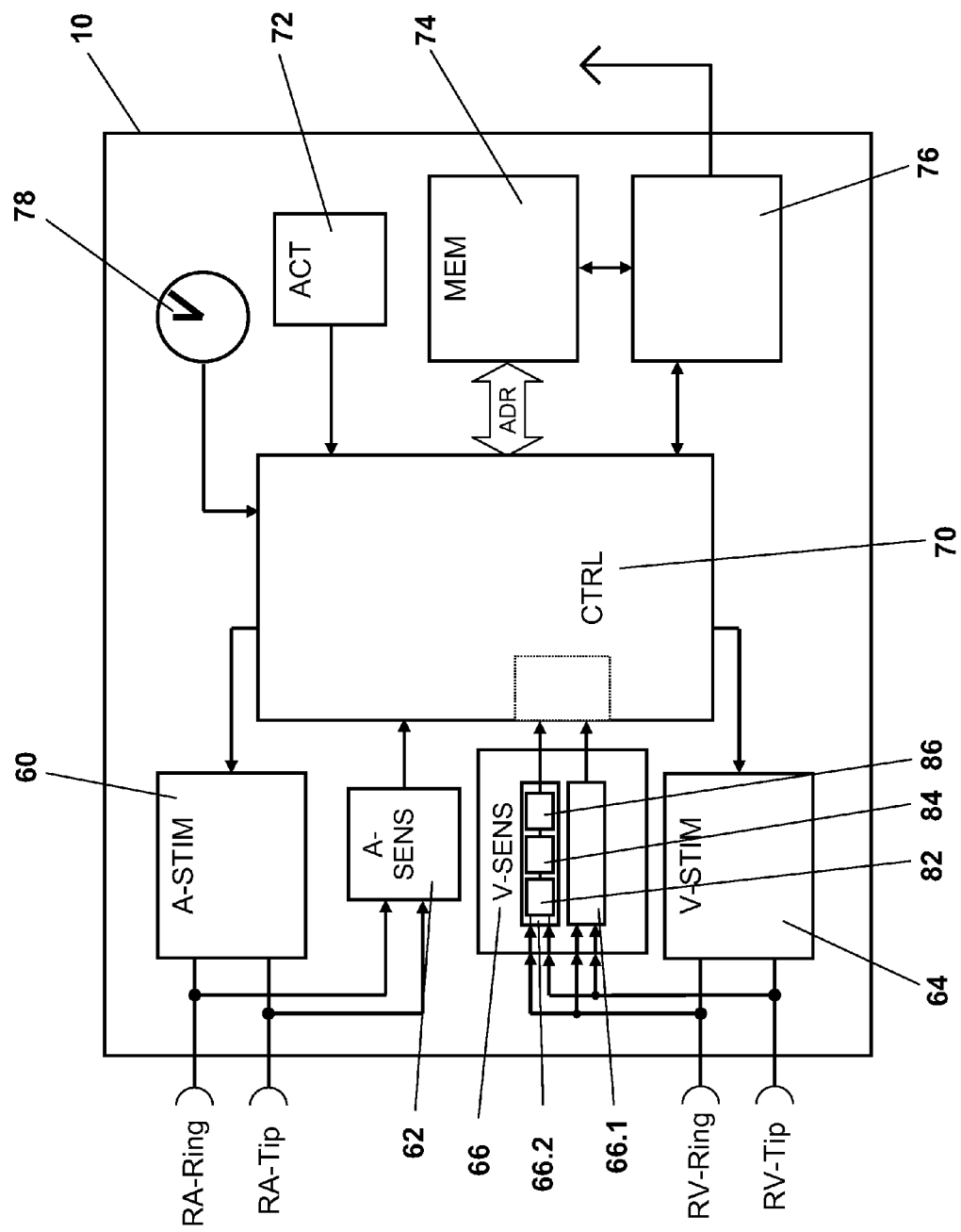
FIG. 2 is a schematic block diagram of the implantable medical device.

FIG. 2 shows the schematic block diagram of the implantable medical device 10. Atrial electrode lead 14 is connected to an atrial stimulation unit 60 and an atrial sensing unit 62. Ventricular electrode lead 16 is connected to a ventricular stimulation unit 64 and a ventricular sensing unit 66. Both the atrial stimulation unit 60 and the ventricular stimulation unit 64 are adapted to generate atrial or ventricular stimulation pulses, respectively, for stimulation of the respective heart chamber. The atrial sensing unit 62 and the ventricular sensing unit 66 are adapted to process electric potentials picked up via a pair of atrial electrodes 18 and 20 or the pair of ventricular electrodes 22 and 24, respectively. Atrial electrode 18 and atrial electrode 20 is a right atrial ventricular electrode. Similarly, ventricular electrode 22 is a right ventricular tip electrode and electrode 24 is a right ventricular ring electrode.

Atrial stimulation unit 60, atrial sensing unit 62, ventricular stimulation unit 64 and ventricular sensing unit 66 are connected to a control unit 70 of the implantable medical device 10. Control unit 70 is further connected to an activity sensor 72 which, for example, can be an accelerometer. Further, control unit 70 is connected to a timer 78 providing a time signal. Control unit 70 is also connected to a memory 74 that can serve for storing data, such as data representing electrograms or programs controlling control unit 70. Finally, control unit 70 is connected to a telemetry unit 76 that is adapted to allow wireless data communication between implantable medical device 10 and the external device 30 (see FIG. 1).

The ventricular sensing unit 66 features two processing channels 66.1 and 66.2. The first processing channel comprises sampling stage 80 that is adapted to sample a picked up myocardial electric signal at a fixed sampling rate that has been determined from the frequency content of the cardiac signal, e.g. 256 Hz. The first processing channel is further adapted to process picked-up electric potentials, so as to generate an electrogram signal in a conventional manner. This signal is fed to control unit 70.

The second processing channel comprises a high frequency sampling stage 82 for sampling the picked-up myocardial electric signals with a second sampling rate, e.g. 4-30 kHz, that is higher than the first sampling rate. In particular, for each sampled myocardial electric signal value sampled by the first channel, a pair of sampled myocardial electric signal values are sampled by the high frequency sampling stage with an interval of 30-240 microseconds, corresponding to a sampling rate of 4-30 kHz. The second channel further comprises a differential stage 84 connected to the high frequency sampling stage and being adapted to generate a high frequency sampling output signal, representing the difference between the two values of each pair of sampled myocardial electric signal values. A comparator 86 is connected to the differential stage and is adapted to compare the high frequency sampled signal with a threshold and to generate a noise detection indicator whenever the threshold is exceeded. This signal is fed to control unit 70 in addition to the output signal of the first channel representing an ECG.

It should be appreciated that no continuous sampling of the picked-up myocardial electric signal by the high frequency sampling stage 82 is required for performing the invention. It is sufficient if the high frequency sampling stage 82 generates a pair of high frequency sampled signal values.

Control unit 70 provides a timer (not shown) that is started whenever control unit 70 receives a noise detection indicator from the second channel 66.2 of ventricular sensing unit 66. The timer times a noise detection period. During such noise detection period, the ECG signal received from the first channel 66.1 of ventricular sensing unit 66 is considered to be affected by noise and, thus, treated differently by control 70 than an ECG signal considered being free of noise.

The timer and further means for evaluating the ECG signal could also be part of ventricular sensing unit 66 instead of control unit 70. Thus the ventricular sensing unit 66 itself would be capable to generate marker signals for each detected ventricular event based on a comparison of the noise-free portions of the ECG signal with a detection threshold. Portions of the ECG signal falling into a noise detection period would be excluded from event detection.

The implantable medical device 10 is a hermetically sealed electronic device that can be implanted under the patient's skin to act as a subcutaneous ECG monitor. The ECG is detected using a pair of sensing electrodes, e.g. electrodes 22 and 24, which—in the disclosed example—are intracardiac electrodes. The invention, however, is also applicable to heart monitoring implants that do require electrode leads and that has electrodes, which have no direct contact to the myocardium. In such devices the invention would be particularly beneficial since it allows reliable processing of signals having a low amplitude in environment exhibiting high noise levels. The latter is usually not the case in intracardiac signals.

The picked up myocardial electric signal is fed to the first channel 66.1 and the second channel 66.2 of the ventricular sensing stage 66 simultaneously. In the second channel, measurements are made from the same pair of electrodes but with a different electronic circuit (including sampling stage 82, differential stage 84 and comparator 86), providing what is called the "high frequency sampling output". These measurements (samplings) are made at a repetition rate that is comparable to or less than the sampling rate of the ECG measurements in the first channel. The measurement is carried out using a pair of sampling points with a short interval between them, such as 30-240 microseconds and renders a pair of sampled values. The difference between these values corresponding to a pair of sampling points may then be calculated in order to measure the change of the sensor potential (myocardial potential) over the short interval. In this way, rapidly changing potentials result in a higher number at the output of the high frequency sampling output.

The high frequency sampling output signal is used to determine whether noise is present by assessing whether its value surpasses a pre-defined threshold or not. If the absolute value of the output exceeds the threshold, noise is considered present and a timer is started, which must expire before the noise detection is reset. Based on the value of this noise detection signal quality metric, the subcutaneous ECG data is classified as valid or invalid. Sensed events in valid data are then used to classify arrhythmias without the interference commonly encountered in data that has not been properly validated.

The results of the preceding analyses are accurate measurements of brady/tachycardia episodes, asystolic episodes, periods of invalid data, and episodes of ventricular instability resulting, for instance, from atrial fibrillation. These data are stored in the device's memory 74 and transmitted wirelessly via telemetry unit 76 at programmed intervals to a data collection station for patient monitoring by the physician. Thus, the physician is provided with a regularly scheduled set of data with which to make an accurate assessment of cardiac activity and arrhythmias. These data may be used to schedule office visits for the patient or to change pharmacologic therapies.

Figure 3:
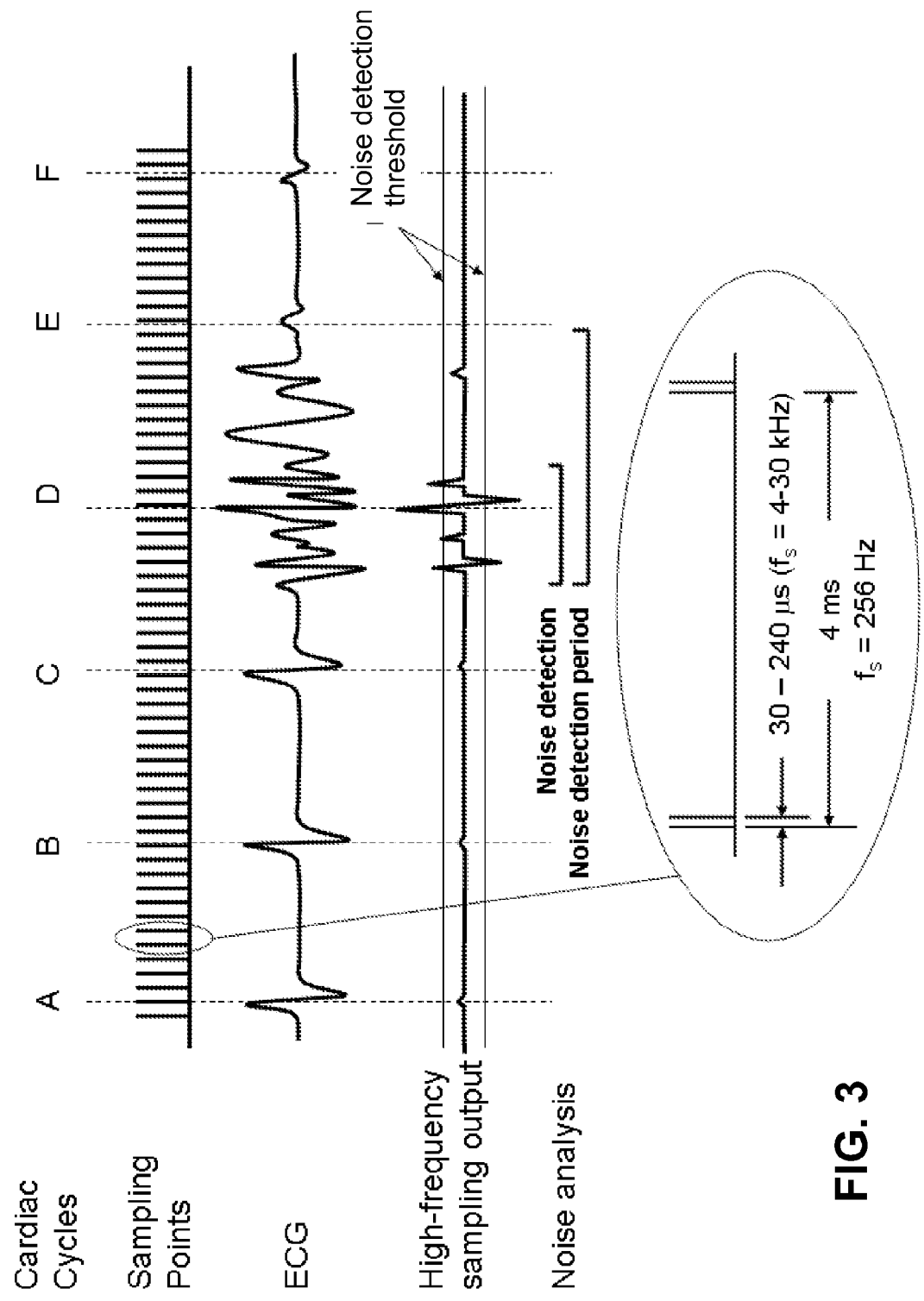
FIG. 3 is an example of a processed picked-up myocardial signal.

One example of a processed picked-up myocardial signal is illustrated in FIG. 3. The numbers indicated in this example are provided in order to provide a comparative illustration only.

In the first row of FIG. 3, cardiac cycles are denoted with A, B, C, D, E and F. In the second line, sampling points are indicated. Sampling points are points in time, where sampling of the input signal—the myocardial electric signal—is performed in the first channel.

The third row of FIG. 3 represents an intracardiac electrogram (ECG) that is acquired by the first channel 66.1 of the sensing unit 66.

The fourth line of FIG. 3 depicts the high-frequency sampling output signal generated in the second channel 66.2 of ventricular sensing unit 66. The signal depicted in line 4 of FIG. 3 represents the difference between two sampling values for each sampling point of line 2 of FIG. 3. These two sampling values forming a pair of high-frequency sampled myocardial electric signal values are sampled in an interval of 30 to 240 μs duration. These pairs of sampling values are taken at a frequency comparable to the first sampling rate, corresponding to the sampling points in line 2 FIG. 3. The detailed illustration at the bottom of FIG. 3 illustrates that the sampling points in line 2 of FIG. 3 are spaced apart in time by 4 ms (corresponding to a sampling rate of 256 Hz). The detail given at the bottom of FIG. 3 further shows that for each of the sampling points in line 1 corresponding to the sampling rate of the first channel, two sampling points corresponding to a much higher sampling rate of 4 to 30 kHz are provided in the second channel.

The fifth line of FIG. 3 illustrates time windows corresponding to noise detection.

In the example given in FIG. 3, cardiac cycles A, B, and C are of sufficient amplitude to be detected easily, using only ECG data, and there is no noise present in the signal. However, the ECG signal corresponding to cycle D is corrupted by noise that could be due to myopotentials or transient and intermittent loss of contact with the sensing electrodes of the implanted device. This could result in over-sensing of the ECG signal and classification as tachycardia or arrhythmia.

However, the high frequency sampling output signal (line 4 of FIG. 3) captures this noise, and when it crosses a programmed threshold, it provides a noise detection indicator. When this noise detection occurs, subsequent interpretation of QRS complexes within the ECG is either suspended or is subject to increased scrutiny until noise is no longer detected and a preset timer (Noise Detection Period) has expired. After the noise episode, small amplitude QRS complexes (E and F) could be detected with a low programmed threshold and without fear of incorrectly sensing noise.

Although an exemplary embodiment of the present invention has been shown and described, it should be apparent to those of ordinary skill that a number of changes and modifications to the invention may be made without departing from the spirit and scope of the invention. In particular, it is possible to apply the concept of noise detection to other signals than ventricular signal or myocardial signal in general. This invention can readily be adapted to a number of different kinds of medical devices by following the present teachings. All such changes, modifications and alterations should therefore be recognized as falling within the scope of the present invention.

What is claimed is:

1. A heart monitor comprising:
an electric signal acquisition and processing stage;
two implantable electrodes configured to pick up myocardial electric signals;
said electric signal acquisition and processing stage connected or being connectable to the two implantable electrodes;
said electric signal acquisition and processing stage comprising a first channel and a second channel that are utilized as signal processing channels;
said first channel comprising
a first sampling stage configured to sample picked-up myocardial electric signals at a first sampling rate, said first channel configured to process the picked-up myocardial electric signals and generate an electrogram signal;
said second channel comprising
a high frequency sampling stage configured to sample at least portions of said picked-up myocardial electric signals at a second sampling rate to detect noise, wherein said second sampling rate is higher than said first sampling rate and wherein said sample picked-up myocardial electric signals at said first sampling rate and said sample at least portions of said picked-up myocardial electric signals at said second sampling rate occur in parallel to effectively sample each of said picked-up myocardial electric signals at a plurality of different time intervals;
a differential stage configured to generate a high frequency sampled output signal that represents a difference between two consecutive high frequency sampled myocardial electric signal values; and,
a comparator that is configured to compare said high frequency sampled output signal with a threshold and to generate a noise detection indicator whenever said threshold is exceeded.

2. The heart monitor according to claim 1, wherein said second channel is configured to generate pairs of high frequency sampled myocardial electric signal values with a repetition rate that is different than said second sampling rate.

3. The heart monitor according to claim 1, wherein said second channel is configured to generate pairs of high frequency sampled myocardial electric signal values with a repetition rate that corresponds to said first sampling rate, so that one pair of high frequency sampled myocardial electric signal values is generated for each sampled myocardial electric signal value generated by the first channel.

4. The heart monitor according to claim 1 further comprising a timer that is triggered whenever the high frequency sampled signal exceeds the threshold.

5. The heart monitor according to claim 4, wherein said timer times a preset noise detection period, during which an ECG signal generated in said first channel is evaluated differently than otherwise.

6. The heart monitor according to claim 1 wherein said first sampling rate is between 200 and 300 Hz.

7. The heart monitor according to claim 1, wherein said second sampling rate is between 4 to 30 kHz.

8. A method for processing electric signals representing a time course of myocardial potentials comprising:
sampling a physiologic signal in a first channel with a first sampling rate;
simultaneously sampling the physiologic signal in a second channel with a second sampling rate that is higher than said first sampling rate;
forming a difference between two sampling values taken from said second channel;
comparing said difference with a threshold;
generating a noise detection indicator whenever said threshold is exceeded wherein said sampling, simultaneously sampling, forming, comparing and generating are accomplished with a heart monitor comprising
an electric signal acquisition and processing stage;
two implantable electrodes configured to pick up said physiologic signal comprising myocardial electric signals;
said electric signal acquisition and processing stage connected or being connectable to the two implantable electrodes;
said electric signal acquisition and processing stage comprising a first channel and a second channel that are utilized as signal processing channels;
said first channel comprising a first sampling stage configured to sample picked-up myocardial electric signals at said first sampling rate, said first channel configured to process the picked-up myocardial electric signals and generate an electrogram signal;

said second channel comprising a high frequency sampling stage configured to sample at least portions of said picked-up myocardial electric signals at said second sampling rate to detect noise, wherein said second sampling rate is higher than said first sampling rate and wherein said sample picked-up myocardial electric signals at said first sampling rate and said sample at least portions of said picked-up myocardial electric signals at said second sampling rate occur in parallel to effectively sample each of said picked-up myocardial electric signals at a plurality of different time intervals;

a differential stage configured to generate a high frequency sampled output signal that represents said difference between two consecutive high frequency sampled myocardial electric signal values; and, a comparator that is configured to compare said high frequency sampled output signal with said threshold and to generate said noise detection indicator whenever said threshold is exceeded.

9. The method according to claim 8, wherein the physiologic signal comprises at least one sampled myocardial electric signal value and for each sampled myocardial electric signal value generated in the first channel, a pair of high frequency sampled myocardial electric signal values is generated in the second channel.

10. The method according to claim 8 wherein a noise detection period is started whenever said difference exceeds said threshold.

11. A heart monitor comprising:

an electric signal acquisition and processing stage;

two implantable electrodes configured to pick up myocardial electric signals;

said electric signal acquisition and processing stage connected or being connectable to the two implantable electrodes;

said electric signal acquisition and processing stage comprising a first channel and a second channel that are utilized as signal processing channels;

said first channel comprising a first sampling stage configured to sample picked-up myocardial electric signals at a first sampling rate, said first channel configured to process the picked-up myocardial electric signals and generate an electrogram signal;

said second channel comprising a high frequency sampling stage configured to sample at least portions of said picked-up myocardial electric signals at a second sampling rate to detect noise, wherein said second sampling rate is higher than said first sampling rate and wherein a number of samples per second obtained at said second sampling rate is less than the sampling rate per second so that high frequency sampling does not occur continuously at said second sampling rate and wherein said sample picked-up myocardial electric signals at said first sampling rate and said sample at least portions of said picked-up myocardial electric signals at said second sampling rate occur in parallel to effectively sample each of said picked-up myocardial electric signals at a plurality of different time intervals;

a differential stage configured to generate a high frequency sampled output signal that represents a difference between two consecutive high frequency sampled myocardial electric signal values; and, a comparator that is configured to compare said high frequency sampled output signal with a threshold and to generate a noise detection indicator whenever said threshold is exceeded.

12. The heart monitor according to claim 11, wherein said second channel is configured to generate pairs of high frequency sampled myocardial electric signal values with a repetition rate that is different than said second sampling rate.

13. The heart monitor according to claim 11, wherein said second channel is configured to generate pairs of high frequency sampled myocardial electric signal values with a repetition rate that corresponds to said first sampling rate, so that one pair of high frequency sampled myocardial electric signal values is generated for each sampled myocardial electric signal value generated by the first channel.

14. The heart monitor according to claim 11 further comprising a timer that is triggered whenever the high frequency sampled signal exceeds the threshold.

15. The heart monitor according to claim 14, wherein said timer times a preset noise detection period, during which an ECG signal generated in said first channel is evaluated differently than otherwise.

16. The heart monitor according to claim 11 wherein said first sampling rate is between 200 and 300 Hz.

17. The heart monitor according to claim 11, wherein said second sampling rate is between 4 to 30 kHz.

* * * * *